(12) United States Patent
Brown et al.

(10) Patent No.: US 8,481,004 B2
(45) Date of Patent: Jul. 9, 2013

(54) STANNOUS SALT AND SODIUM TRIPOLYPHOSPHATE ORAL CARE COMPOSITIONS AND METHODS

(75) Inventors: James R. Brown, Edison, NJ (US); Linh Fruge, Hillsborough, NJ (US); Tao Xu, Newtown, MA (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 1175 days.

(21) Appl. No.: 12/094,817

(22) PCT Filed: Nov. 21, 2006

(86) PCT No.: PCT/US2006/061134
§ 371 (c)(1),
(2), (4) Date: May 23, 2008

(87) PCT Pub. No.: WO2007/062365
PCT Pub. Date: May 31, 2007

(65) Prior Publication Data
US 2008/0286214 A1 Nov. 20, 2008

Related U.S. Application Data

(60) Provisional application No. 60/739,130, filed on Nov. 23, 2005.

(51) Int. Cl.
*A61K 8/00* (2006.01)
*A61K 6/00* (2006.01)
*A61Q 11/00* (2006.01)

(52) U.S. Cl.
USPC ............... 424/49; 424/52; 424/57; 424/401; 433/216

(58) Field of Classification Search
USPC .................. 424/401, 49, 52, 57; 433/216
See application file for complete search history.

(56) References Cited

U.S. PATENT DOCUMENTS

| 4,528,180 A * | 7/1985 | Schaeffer .................. 424/52 |
|---|---|---|
| 4,627,977 A | 12/1986 | Gaffar et al. |
| 4,961,924 A | 10/1990 | Suhonen |
| 5,017,362 A * | 5/1991 | Gaffar et al. .................. 424/52 |
| 5,017,363 A | 5/1991 | Suhonen |
| 5,487,906 A | 1/1996 | Dixit et al. |
| 5,578,293 A | 11/1996 | Prencipe et al. |
| 5,716,600 A | 2/1998 | Zahradnik et al. |
| 5,776,435 A | 7/1998 | Gaffar et al. |
| 6,350,436 B1 | 2/2002 | Glandorf et al. |
| 6,447,756 B1 | 9/2002 | Dixit et al. |
| 6,521,216 B1 | 2/2003 | Glandorf et al. |
| 6,652,841 B1 * | 11/2003 | Brown et al. .................. 424/49 |
| 7,063,833 B2 | 6/2006 | Glandorf et al. |
| 2003/0211054 A1 | 11/2003 | Szeles et al. |
| 2005/0112070 A1 | 5/2005 | Glandorf et al. |

FOREIGN PATENT DOCUMENTS

| CA | 2068431 | 5/1991 |
|---|---|---|
| CA | 2271302 | 5/1998 |
| CA | 2468606 | 6/2003 |
| EP | 0397452 | 11/1990 |
| EP | 0469722 | 2/1992 |
| WO | WO 98/051271 | 11/1998 |
| WO | WO 01/34108 | 5/2001 |
| WO | WO 02/02128 | 1/2002 |
| WO | 02092038 A2 | 11/2002 |
| WO | WO 03/006320 | 1/2003 |

OTHER PUBLICATIONS

Chinese Application 200680051300.6—Office Action dated Mar. 23, 2010.
International Search Report and Written Opinion in Inteniation Application No. PCT/US06/061134, mailed Jun. 25, 2007.

* cited by examiner

*Primary Examiner* — Lezah Roberts
(74) *Attorney, Agent, or Firm* — Howard C. Lee

(57) ABSTRACT

Oral care compositions containing a stannous salt and sodium tripolyphosphate are provided where stannous tripolyphosphate ionic intermediates comprise less than about 1% of the compositions Tetrasodium pyrophosphate, a methylvinyl ether-maleic anhydride copolymer and/or a silica oral polishing agent may be added for further efficacy. In a single phase blend, the oral care composition may be effectively limited to comprise less than about 10% water. In a dual-phase blend a mixture having the stannous salt in a first phase and the sodium tripolyphosphate in a second phase may be generated from a dual chamber storage tube (with each phase provided from a separate chamber) immediately prior to dental care usage.

18 Claims, No Drawings

STANNOUS SALT AND SODIUM TRIPOLYPHOSPHATE ORAL CARE COMPOSITIONS AND METHODS

CROSS-REFERENCE TO RELATED APPLICATION

This present application claims benefit of U.S. Provisional Patent Application No. 60/739,130 filed Nov. 23, 2005, the contents of which are hereby incorporated by reference in its entirety.

BACKGROUND OF THE INVENTION

Stannous salts such as stannous fluoride are used in dentifrices as agents for preventing plaque. However, some disadvantages of stannous salts include instability, tendency to stain teeth, astringency and unpleasant taste for users. For that reason, oral care compositions containing stannous salts such as stannous fluoride are often presented as dual phase compositions, in which the stannous salt is kept separate from the other components in order to reduce its negative effects on the oral cavity, such as astringency and unpleasant taste. See, e.g., U.S. Pat. No. 6,521,216 and U.S. Pat. No. 7,063,833, both to Glandorf et al.

Sodium tripolyphosphate is an effective anticalculus (antitartar) agent, but the compound is not generally compatible with stannous salts in long term storage (such as that normally sustained in the lifetime of a tube of toothpaste between time of packaging and time of discard after use). In particular, the combination of sodium tripolyphosphate with stannous salts such as stannous fluoride can lead to undesirable stannous tripolyphosphate intermediates.

Accordingly, there is an ongoing need for oral care compositions that have improved efficacy in combating plaque and tooth discoloration and are still able to retain long-term stability.

BRIEF SUMMARY OF THE INVENTION

An oral care composition comprising:
(a) about 0.01 to about 5% stannous salt;
(b) about 0.01 to about 15% sodium tripolyphosphate;
(c) less than about 10% by weight water; and
(d) about 0.1 to about 15% by weight of a methylvinyl ether-maleic anhydride copolymer;
wherein the composition comprises less than about 1% of stannous tripolyphosphate ionic intermediates.

A dual-phase oral care composition comprising:
(a) a first phase comprising about 0.01 to about 5% stannous salt in a first orally acceptable vehicle; and
(b) a second phase comprising about 0.01 to about 15% sodium tripolyphosphate in a second orally acceptable vehicle;
wherein the first phase is in fluid interface with the second phase, and wherein the total water concentration in the oral care composition is less than about 10%.

A method for making an oral care composition, comprising blending: (a) about 0.01 to about 5% stannous salt; (b) about 0.01 to about 15% sodium tripolyphosphate; and (c) about 0.1 to about 5% of a methylvinyl ether-maleic anhydride copolymer.

An oral care kit comprising a container containing a mixture of: (a) about 0.01 to about 5% stannous salt; (b) about 0.01 to about 15% sodium tripolyphosphate; and (c) less than about 10% by weight water; wherein the comprises less than about 1% stannous tripolyphosphate ionic intermediates.

An oral care kit, comprising:
(a) a first chamber having a first outlet in fluid communication with the first chamber for discharge of a first dentifrice from the first chamber; and
(b) a second chamber having a second outlet in fluid communication with the second chamber for discharge of a second dentifrice from the second chamber:
wherein the first dentifrice comprises about 0.01 to about 5% stannous salt in a first orally acceptable vehicle, the second dentifrice comprises about 0.01 to about 15% sodium tripolyphosphate and about 0.1 to about 15% of a methylvinyl ether-maleic anhydride copolymer in a second orally acceptable vehicle, and
wherein the second outlet is proximate to the first outlet so that, during simultaneous discharge of the first dentifrice from the first chamber through the first outlet and of the second dentifrice from the second chamber through the second outlet, discharged first dentifrice fluidly interfaces with discharged second dentifrice to form a mixture in which the discharged first dentifrice provides at least one first portion of the mixture and the discharged second dentifrice provides at least one second portion of the mixture.

A method for cleaning the surface of a tooth comprising the step of applying a composition comprising:
(a) about 0.01 to about 5% stannous salt;
(b) about 0.01 to about 15% sodium tripolyphosphate;
(c) less than about 10% by weight water; and
(d) about 0.1 to about 15% by weight of a methylvinyl ether-maleic anhydride copolymer;
wherein the composition comprises less than about 1% stannous tripolyphosphate ionic intermediates, to the surface.

A method for maintaining systemic health of a human or mammal comprising the step of applying a composition comprising:
(a) about 0.01 to about 5% stannous salt;
(b) about 0.01 to about 15% sodium tripolyphosphate;
(c) less than about 10% by weight water, and
(d) about 0.1 to about 15% by weight of a methylvinyl ether-maleic anhydride copolymer;
wherein the composition comprises less than about 1% stannous tripolyphosphate ionic intermediates, to the oral surfaces of the human or mammal.

DETAILED DESCRIPTION OF THE INVENTION

As used throughout the present disclosure, ranges are a shorthand for describing each and every value within the range. Any value within the range can be selected as the terminus of the range. In addition, all references cited in the present disclosure are hereby incorporated by reference in their entireties. Where there is any conflict between definitions in the disclosures of the references cited and the present disclosure, the present disclosure is controlling.

In certain embodiments, the invention is directed to a dual phase composition and oral care kit wherein stannous salt and sodium tripoly phosphate are formulated to be physically separated in two separate aqueous mixtures. Each of the two aqueous mixtures is stored in a physically separate chamber (such as in a dual-compartment tube of toothpaste), and the two aqueous mixtures are blended together into a mixture when the anticipated time between mixture formation and application of the mixture to the teeth is sufficiently minimal such that the reaction time needed for migration of the stannous ion and the tripolyphosphate ionic complex into an ionic intermediate configuration for the stannous tripolyphosphate is not sufficient for stannous tripolyphosphate ionic intermediate formation prior to use.

In certain embodiments, at least one of tetrasodium pyrophosphate, a methylvinyl ether-maleic anhydride copolymer or a silica oral polishing agent may be optionally mixed into the formulation. In certain embodiments, the methylvinyl ether-maleic anhydride copolymer has the structural formula

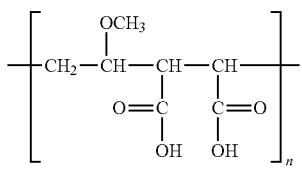

wherein n is an integer that provides molecular weight in the agent of about 60,000 to about 500,000. Examples of suitable methylvinyl ether-maleic anhydride copolymers for the present invention are copolymers of methyl vinyl ether and maleic anhydride available under the trade name Gantrez® (for example, Gantrez® S-96, Gantrez® S-97, Gantrez® MS and MS-955, Gantrez® ES, ES-225 and ES-425 available from International Specialty Products, Wayne, N.J., USA).

In certain embodiments, the present invention provides compositions comprising an orally acceptable carrier or vehicle. As used herein, an "orally acceptable carrier" and "orally acceptable vehicle" are used interchangeably, and refer to a material or combination of materials that is safe for use in the present compositions, commensurate with a reasonable benefit/risk ratio, with which the other ingredients may be associated while retaining significant clinical efficacy. Such carrier materials should be selected for compatibility with the other ingredients of the compositions, and preferably do not substantially reduce the efficacy of the other ingredients. Selection of specific carrier components is dependent on the desired product form, including dentifrices, rinses, gels, and paints.

Materials useful in carriers include but are not limited to: adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof. As used herein, an "adhesion agent" is a material or combination of materials that enhances the retention of an ingredient to an oral cavity surface onto which it is applied. Such adhesion agents include without limitation: adhesives, film forming materials and viscosity enhancers; for example, hydrophilic organic polymers, hydrophobic organic polymers, silicone gums, silicone adhesives, silicas, and combinations thereof.

In certain embodiments, any of tetrasodium pyrophosphate, a methylvinyl ether-maleic anhydride copolymer, and/or a silica oral polishing agent are independently mixed into the oral care composition. In certain embodiments, the silica oral polishing agent is high cleaning silica. In certain embodiments, the stannous salt comprises a stannous halide such as stannous fluoride, stannous chloride dehydrate; organic stannous carboxylate salts such as stannous formate, acetate, gluconate, lactate, tartrate, oxalate, malonate and citrate; stannous ethylene glyoxide, and mixtures thereof. One or more stannous salts are optionally present in a total amount of about 0.01% to about 5%, optionally about 0.05 to about 4%, about 0.1 to about 3%, about 0.5 to about 2% or about 0.1 to about 1%.

In certain embodiments, the oral care composition comprises a mixture having:

(a) a first phase comprising a first orally acceptable aqueous vehicle; and
(b) a second phase comprising a second orally acceptable aqueous vehicle; where a stannous salt is mixed into the first orally acceptable aqueous vehicle, sodium tripolyphosphate is mixed into the second orally acceptable aqueous vehicle; and the first phase provides at least one first portion of the mixture, the second phase provides at least one second portion of the mixture, and at least one of the first portion is in fluid interface with at least one of the second portion in the mixture.

In certain embodiments, any of tetrasodium pyrophosphate and/or a silica oral polishing agent (such as high cleaning silica) may be independently mixed in at least one phase of the first phase and the second phase. In certain embodiments of the mixture, a methylvinyl ether-maleic anhydride copolymer, such as that of Formula I, is mixed in the second phase.

In certain embodiments, the present invention is directed to methods comprising:

(a) mixing about 0.01 to about 5% stannous salt into a first orally acceptable aqueous vehicle to provide a first phase;
(b) mixing about 0.01 to about 15% sodium tripolyphosphate into a second orally acceptable aqueous vehicle to provide a second phase;
(c) storing the first phase in a first enclosure:
(d) storing the second phase in a second enclosure; and
(e) removing the first phase from the first enclosure and removing the second phase from the second enclosure so that the first phase and the second phase together provide the mixture.

In certain embodiments, the invention further provides a first type of oral care kit as a container containing a mixture of (a) about 0.01 to about 5% stannous salt; and
(b) about 0.01 to about 15% sodium tripolyphosphate;
wherein the mixture comprises less than about 1% stannous tripolyphosphate ionic intermediates and comprises less than about 10% water.

In certain embodiments, the invention provides a second type of oral care kit, comprising:

(a) a first chamber having a first outlet in fluid communication with the first chamber for discharge of a first dentifrice from the first chamber; and
(b) a second chamber having a second outlet in fluid communication with the second chamber for discharge of a second dentifrice from the second chamber;
wherein the first dentifrice comprises stannous salt in a first orally acceptable vehicle, the second dentifrice comprises sodium tripolyphosphate in a second orally acceptable vehicle, and the second outlet is proximate to the first outlet so that, during simultaneous discharge of the first dentifrice from the first chamber through the first outlet and of the second dentifrice from the second chamber through the second outlet, the discharged first dentifrice interfaces with discharged second dentifrice to form a mixture.

Thickening agents useful for the present invention include, without limitation: carboxyvinyl polymers, carrageenans (also known as Irish moss and more particularly iota-carrageenan), cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica, and mixtures thereof.

Viscosity modifiers useful for the present invention include, without limitation: mineral oil, petrolatum, clays and organomodified clays, silica, and mixtures thereof. In various embodiments, the viscosity modifiers are able to inhibit settling or separation of ingredients, or to promote redispersibility upon agitation of a liquid composition.

Diluents useful for the present invention include, without limitation, materials or combinations of materials that can solubilize and/or suspend other components. In various embodiments, diluents can adjust the viscosity of the composition, optionally in conjunction with viscosity modifiers as discussed herein and other components of the composition.

Surfactants useful for the present invention include, without limitation: anionic, nonionic, and amphoteric surfactants. Surfactants may be used, for example, to provide enhanced stability of the formulation, to help in cleaning the oral cavity surfaces through detergency, and to provide foam upon agitation, e.g., during brushing. Suitable anionic surfactants include, e.g., water-soluble salts of $C_{8-20}$ alkyl sulfates, sulfonated monoglycerides of $C_{8-20}$ fatty acids, sarcosinates, taurates; e.g., sodium lauryl sulfate, sodium coconut monoglyceride sulfonate, sodium lauryl sarcosinate, sodium lauryl isoethionate, sodium laureth carboxylate and sodium dodecyl benzenesulfonate, and mixtures thereof. Suitable nonionic surfactants include, e.g., poloxamers, polyoxyethylene sorbitan esters, fatty alcohol ethoxylates, alkylphenol ethoxylates, tertiary amine oxides, tertiary phosphine oxides, dialkyl sulfoxides, and mixtures thereof.

Foam modulators useful for the present invention include, without limitation: materials operable to increase amount, thickness or stability of foam generated by the composition (e.g., dentifrice compositions) upon agitation. Any orally acceptable foam modulator can be used, including polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. One or more PEGs are optionally present in a total amount of about 0.1% to about 10%, for example about 0.2% to about 5% or about 0.25% to about 2%.

Humectants useful for the present invention include, without limitation: polyhydric alcohols such as glycerin, sorbitol, xylitol or low molecular weight PEGs. In various embodiments, humectants can prevent hardening of paste or gel compositions upon exposure to air. In various embodiments humectants also function as sweeteners.

In certain embodiments directed to a two-phase oral care composition having a stannous salt in a first phase and sodium tripolyphosphate in a second phase, the measured pH of the first phase is sustained at about 2 to about 8, and the measured pH of the second phase is sustained at about 5 to about 11. The embodiments, therefore, provide an effectively acid pH (a chemical pH of about 7 or less) in the first phase with a measured pH (the pH measured when a pH probe is inserted into the phase) of between about 2 and about 8 and an effectively alkaline pH (a chemical pH of between about 7 and about 11) in the second phase with a measured pH (again, the pH measured when a pH probe is inserted into the phase) of between about 5 and about 1.

Any other desired components may be added to the compositions, including, for example, mouth-feel agents, pH modifying agents, flavorants, sweeteners, additional anticalculus and antiplaque agents, abrasives, polishing agents, antimicrobial (e.g., antibacterial) agents such as those described in U.S. Pat. No. 5,776,435, saliva stimulants, anti-inflammatory agents, $H_2$ antagonists, nutrients, vitamins, proteins, antioxidants, colorants, or additional active materials useful for the prevention or treatment of a condition or disorder of hard or soft tissue of the oral cavity, the prevention or treatment of a physiological disorder or condition, or to provide a cosmetic benefit.

Certain embodiments provide oral care compositions having stannous salt and sodium tripolyphosphate in a first phase comprising a first orally acceptable aqueous vehicle and in a second phase comprising a second orally acceptable aqueous vehicle. The first and second phases may be independently formulated such that the stannous salt is mixed into the first orally acceptable aqueous vehicle and such that the sodium tripolyphosphate is mixed into the second orally acceptable aqueous vehicle. The first phase may be maintained at a measured pH of about 2 to about 8, and the second phase may be maintained at a measured pH of about 5 to about 11. The first and second phases may be kept from physical chemical interaction prior to a brief period prior to application to a tooth surface. At that time, the first and second phases may be combined together (e.g. on a toothbrush) as a mixture (a combination of different components) where the first phase provides at least one first portion of the mixture, the second phase provides at least one second portion of the mixture, and the at least one first portion is in fluid interface with the at least one second portion in the mixture. This may be achieved by, for example, use of a dual-compartment toothpaste tube where two approximately equivalent volumetric portions from each of the two compartments are simultaneously extruded onto a toothbrush under the presumption that the resulting mixture dentifrice is to be immediately applied to the teeth by the user.

In certain embodiments, a two-phase mixture provides an oral care composition having stannous fluoride as the stannous salt and sodium tripolyphosphate in differentiated phases where the first phase is mixed to comprise a measured pH of about 2 to about 8. In various embodiments, this first phase and the second phase each may additionally comprise one or more ingredients chosen from citric acid, trisodium citrate dihydrate, an additional stannous salt, glycerine, a cellulosic polymer such as, e.g., sodium carboxymethyl cellulose (Sodium CMC 2000), a gum such as xanthan gum or carrageenan gum (e.g., iota carrageenan), a flavorant (such as, e.g., the sweeteners sodium saccharin or sorbitol) an additional salt such as, e.g., tetrasodium pyrophosphate, polymer such as, e.g. polyoxypropylene-polyoxyethylene block polymer (PLURONIC® F127), titanium dioxide, an oil such as, e.g., castor oil, silicon dioxide, precipitated silica, synthetic amorphous silica, or sodium lauryl sulfate.

In various embodiments, the compositions comprise, further to the first phase described in (a) above, a second phase (b) which is mixed to comprise a measured pH about 5 to about 11.

The compositions of the present invention optionally comprise silica oral polishing agent ("silica abrasive") in at least one of the phases. In various embodiments, silica may be mixed at, for example, about 10 to about 50%, about 15 to about 40% or about 20 to about 30% dental type precipitated amorphous hydrated silicon dioxide; and at about 10 to about 15%, about 11 to about 14 and about 12 to about 13% synthetic amorphous silica.

In the dual phase mixture embodiments having at least two portions where each is extruded from an independently stored phase, silica may be provided in the first phase as about 10 to about 50% dental type precipitated amorphous hydrated silicon dioxide, less than about 8% synthetic amorphous precipitated silica, less than about 15% synthetic amorphous silica. In the second phase, in various embodiments silica may be provided in an amount of about 10 to about 50% precipitated synthetic amorphous silica, less than about 15% synthetic amorphous silica, or less than about 8% synthetic amorphous precipitated silica.

In various embodiments, the compositions comprise silica in the form of silica gel, hydrated silica or precipitated silica, alumina, insoluble phosphates, calcium carbonate, resinous abrasives such as urea-formaldehyde condensation products, and mixtures thereof. Insoluble phosphates useful as abrasives include, for example, orthophosphates, polymetaphosphates and pyrophosphates; e.g., dicalcium orthophosphate dihydrate, calcium pyrophosphate, dicalcium pyrophosphate, tricalcium phosphate, calcium polymetaphosphate and insoluble sodium polymetaphosphate or mixtures thereof. One or more abrasives are optionally present in an abrasive effective total amount of, in various embodiments, about 5% to about 70%, about 10% to about 50%, or about 15% to about 30% by weight of the composition. Average particle size of an abrasive, if present, is generally about 0.1 to about 30 microns, for example about 1 to about 20 microns or about 5 to about 15 microns. The use of silica as previously noted is preferred to reduce staining of the teeth due to the stannous fluoride.

In various embodiments, the present methods include adding and mixing the ingredients in a suitable vessel such as a stainless steel tank provided with a mixer. In certain embodiments, the stannous salt is mixed into a first orally acceptable aqueous vehicle to provide a first phase of a dentifrice; the sodium tripolyphosphate is mixed into a second orally acceptable aqueous vehicle to provide a second phase of the dentifrice; the first phase is stored in a first enclosure; the second phase is stored in a second enclosure; and the first phase is expelled from the first enclosure and the second phase is expelled from the second enclosure just prior to application to the teeth so that the first phase and the second phase together provide a mixture. In various embodiments, the resultant mixture has at least one first portion comprising the first phase, the mixture has at least one the second portion comprising the second phase, and each first portion is in fluid interface with at least one second portion.

In various embodiments, the mixture may be provided to the consumer in the form of an oral care kit providing (a) a first chamber (the first storage enclosure for storing the first phase of the mixture) having a first outlet in fluid communication with the first chamber for discharge of a first dentifrice from the first chamber; and (b) a second chamber (the second storage enclosure for storing the second phase of the mixture) having a second outlet in fluid communication with the second chamber for discharge of a second dentifrice from the second chamber. In various embodiments, the second outlet is proximate to the first outlet so that, during simultaneous discharge of the first dentifrice from the first chamber through the first outlet and of the second dentifrice from the second chamber through the second outlet, discharged first dentifrice fluidly interfaces with discharged second dentifrice to form the mixture. In certain embodiments, equal amounts of each phase are delivered into the mixture so that the consumer has a convenient basis for ascertaining that both phases are being delivered and that rapid intermixing of the phases will occur as the mixture is brushed against the teeth.

Additional ingredients such as flavorant, coloring or sweeteners are added at any point during the mixing process but in various embodiments such ingredients are preferably added last or close to last.

The present invention also provides methods for treating a tooth surface using compositions according to the present invention. In certain embodiments, the methods comprise applying a composition of the present invention to the tooth surface. As referred to herein, "applying" refers to any method by which a compositional embodiment is placed in contact with the tooth surface. Such methods, in various embodiments, comprise direct application of a composition by such methods as painting and brushing. Suitable application devices include, e.g., toothbrushes.

In one prophetic example, a composition according to the present invention comprises less than about 10% water, and further comprises:
about 0.4 to about 0.8% stannous salt,
about 0.20 to about 24% polyhydric alcohol,
about 10.0 to about 17% amorphous silica,
about 0.5 to about 4% tetrasodium pyrophosphate; and
about 1 to about 15% sodium tripolyphosphate.

In another prophetic example, a composition according to the present invention comprises:
about 0.4 to about 0.8% stannous salt,
about 1 to about 9% water,
about 0.2 to about 24% polyhdric alcohol,
about 0.5 to about 4% tetrasodium pyrophosphate,
about 1 to about 15% sodium tripolyphosphate,
about 10 to about 50% dental type precipitated amorphous hydrated silicon dioxide; and
about 10 to about 17% amorphous silica.

In one prophetic example, the composition comprises stannous fluoride as the stannous salt, and
(i) the first phase is mixed to comprise:
about 0.9 to about 1.8% stannous fluoride,
about 0.3 to about 1% stannous chloride dihydrate,
about 0.5 to about 4% tetrasodium pyrophosphate,
about 10 to about 50% precipitated amorphous hydrated silicon dioxide.
less than about 8% synthetic amorphous precipitated silica,
less than 15% synthetic amorphous silica; and
(ii) the second phase is mixed to comprise:
about 0.5 to about 4% tetrasodium pyrophosphate,
about 0.1 to about 15% methylvinyl ether-maleic anhydride copolymer,
about 1 to about 15% sodium tripolyphosphate,
about 10 to about 50% precipitated synthetic amorphous silica, and
less than about 15% synthetic amorphous silica.

By way of further example, and not limitation, specific embodiments of the present invention are illustrated in the following Examples.

Example 1

A dual component composition of the present invention may be prepared by independently combining the ingredients of "Side 1" and "Side 2" of Table 1:

TABLE I

| Side 1 (Weight %) | (Stannous Portion) |
|---|---|
| q.s. | Purified Water |
| 0.01-2 | Citric Acid Anhydrous |
| 0.5-5 | Trisodium Citrate Dihydrate |
| 0.2-1 | Stannous Fluoride |
| 0.2-2 | Stannous Chloride Dihydrate |
| 20-40 | Glycerin |
| 0.1-5 | Sodium Carboxymethyl Cellulose |
| 0.1-10 | Xanthan Gum |
| 0.1-5 | Sodium Saccharin |
| 0.1-5 | Tetrasodium Pyrophosphate |
| 0.5-10 | Pluronic F127 Polyoxypropylene-Polyoxyethylene Block Polymer |
| 0.1-5 | Titanium Dioxide |
| 0.5-20 | Oil |
| 1-15 | Dental Type Precipitated Amorphous Hydrated Silicon Dioxide |

TABLE I-continued

| | |
|---|---|
| 1-10 | Synthetic Amorphous Precipitated Silica |
| 1-15 | Synthetic Amorphous Silica |
| 1-15 | Sodium lauryl sulfate 30% Solution |
| 0.01-10 | Flavor |

| Side 2 | (Tartar Control Portion) |
|---|---|
| q.s. | Purified Water |
| 0.1-1 | Sodium Saccharin |
| 5-60 | Sorbitol |
| 0.01-5 | Tetrasodium Pyrophosphate |
| 1-15 | Gantrez S-97 13% Liquid |
| 0.5-5 | Sodium Hydroxide 50% |
| 0.01-5 | Titanium Dioxide |
| 1-20 | Glycerine |
| 1-15 | Sodium Tripolyphosphate |
| 0.01-5 | Sodium CMC 2000S-12 Sodium Carboxymethyl Cellulose |
| 0.1-10 | Iota Carrageenan |
| 1-30 | Precipitated Synthetic Amorphous Silica |
| 1-20 | Synthetic Amorphous Silica |
| 1-10 | Sodium lauryl sulfate |
| 0.01-10 | Flavor |

We claim:

1. An oral care composition comprising:
   (a) about 0.01 to about 5% stannous salt;
   (b) about 0.01 to about 15% sodium tripolyphosphate;
   (c) 10% or less water; and
   (d) about 0.1 to about 15% of a methylvinyl ether-maleic anhydride copolymer;
   wherein the composition comprises less than about 1% stannous tripolyphosphate ionic intermediates; and wherein (a), (b), (c) and (d) are blended together.

2. The composition of claim 1, comprising about 0.1 to about 3% stannous salt.

3. The composition of claim 1, comprising about 0.1 to about 10% sodium tripolyphosphate.

4. The oral care composition of claim 1 wherein the stannous salt is stannous fluoride.

5. The composition of claim 1, comprising less than about 8% water.

6. The composition of claim 1, comprising less than about 6% water.

7. The composition of claim 1 further comprising a compound chosen from tetrasodium pyrophosphate and a silica polishing agent.

8. The composition of claim 1 wherein the methylvinyl ether-maleic anhydride copolymer is represented by formula (I):

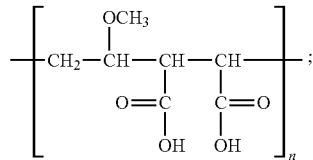

wherein n is an integer that provides a molecular weight of said copolymer of about 60,000 to about 500,000.

9. A method for making an oral care composition of claim 1, comprising blending: (a) 0.01 to about 5% stannous salt; (b) about 0.01 to about 15% sodium tripolyphosphate; and (c) about 0.1 to about 15% of a methylvinyl ether-maleic anhydride copolymer into the composition.

10. An oral care kit comprising a container containing a mixture of: (a) about 0.01 to about 5% stannous salt; (b) about 0.01 to about 15% sodium tripolyphosphate; and (c) 10% or less by weight water; wherein the mixture comprises less than about 1% stannous tripolyphosphate ionic intermediates.

11. The oral care kit of claim 10 wherein the mixture comprises less than about 8% water.

12. The oral care kit of claim 10 wherein the mixture further comprises tetrasodium pyrophosphate.

13. A method for cleaning the surface of a tooth comprising the step of applying a composition according to claim 1 to the surface.

14. A method for maintaining systemic health of a human or mammal comprising the step of applying a composition according to claim 1 to the oral surfaces of the human or mammal.

15. The oral care composition of claim 2, comprising 0.1 to about 10% sodium tripolyphosphate and less than 8% water.

16. The oral care composition of claim 15, wherein the stannous salt is stannous fluoride.

17. The composition of claim 16 wherein the methylvinyl ether-maleic anhydride copolymer is represented by formula (I):

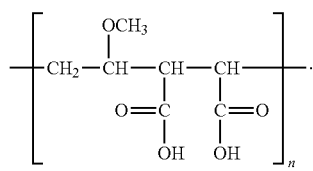

18. The oral care composition of claim 17 further comprising a compound chosen from tetrasodium pyrophosphate and a silica polishing agent.

* * * * *